US006833352B2

(12) United States Patent
Johannessen et al.

(10) Patent No.: US 6,833,352 B2
(45) Date of Patent: Dec. 21, 2004

(54) COAGULATION FACTOR VIIA COMPOSITION

(75) Inventors: Marie Johannessen, Birkerød (DK); Ole Juul Nordfang, Hillerød (DK); Jens Aas Jansen, Charlottenlund (DK)

(73) Assignee: Novo Nordisk Pharmaceuticals, Inc., Princeton, NJ (US)

( * ) Notice: Subject to any disclaimer, the term of this patent is extended or adjusted under 35 U.S.C. 154(b) by 139 days.

(21) Appl. No.: 10/026,032

(22) Filed: Oct. 25, 2001

(65) Prior Publication Data

US 2002/0115590 A1 Aug. 22, 2002

Related U.S. Application Data

(63) Continuation of application No. 09/148,440, filed on Sep. 4, 1998, now Pat. No. 6,310,183.
(60) Provisional application No. 60/059,236, filed on Sep. 18, 1997.

(30) Foreign Application Priority Data

Sep. 10, 1997 (DK) .............................................. 1038/97

(51) Int. Cl.$^7$ ........................ A61K 35/14; A61K 38/00; C07K 14/00
(52) U.S. Cl. ........................... 514/2; 514/802; 514/834; 530/384; 530/350; 530/380; 604/19; 604/48; 604/500
(58) Field of Search ................................ 530/384, 350, 530/380; 604/19, 48, 500; 514/2, 802, 834

(56) References Cited

U.S. PATENT DOCUMENTS

| 4,456,591 A | | 6/1984 | Thomas et al. ............. 424/101 |
| 4,479,938 A | | 10/1984 | Thomas ..................... 424/101 |
| 5,180,583 A | | 1/1993 | Hedner .................... 424/94.64 |
| 5,374,617 A | | 12/1994 | Morrissey et al. ............ 514/8 |
| 5,580,560 A | * | 12/1996 | Nicolaisen et al. ...... 424/94.64 |
| 5,925,739 A | | 7/1999 | Spira et al. ................. 530/383 |

* cited by examiner

Primary Examiner—Jon P. Weber
Assistant Examiner—Holly Schnizer
(74) Attorney, Agent, or Firm—Reza Green; Zen Smith; Richard Bork

(57) ABSTRACT

The invention relates to a pharmaceutical composition comprising Factor VIIa for subcutan, intramuscular or interdermal administration.

Factor VIIa administered subcutanously, intramuscularly or intradermally shows a sufficient transport into the bloodstream in biologically active form and in adequate concentrations, and favorable pharmacokinetic properties.

10 Claims, 4 Drawing Sheets

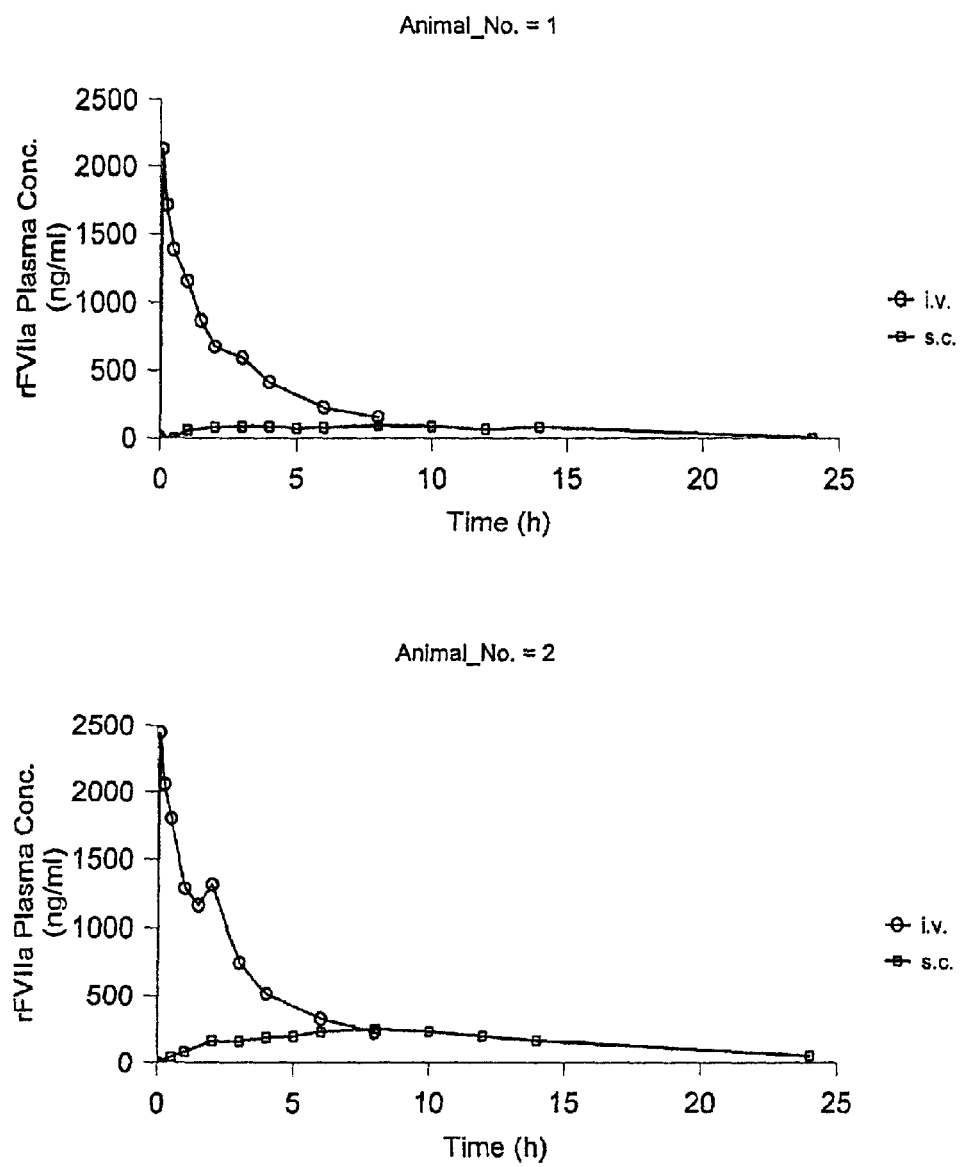
Figure 1. Individual Plasma Concentration Profiles of rFVIIa Following Intravenous (i.v.) and Subcutanous (s.c.) Administration of 0.2 mg/kg to Minipigs

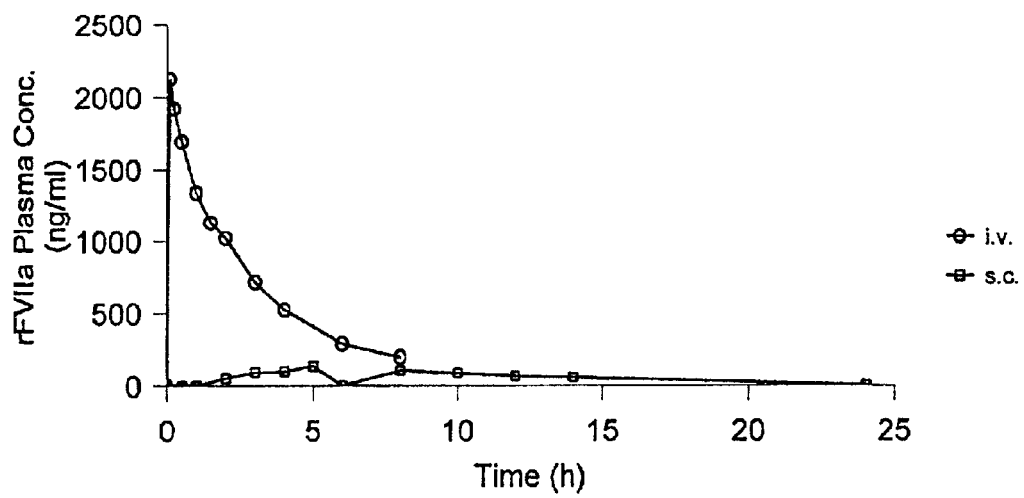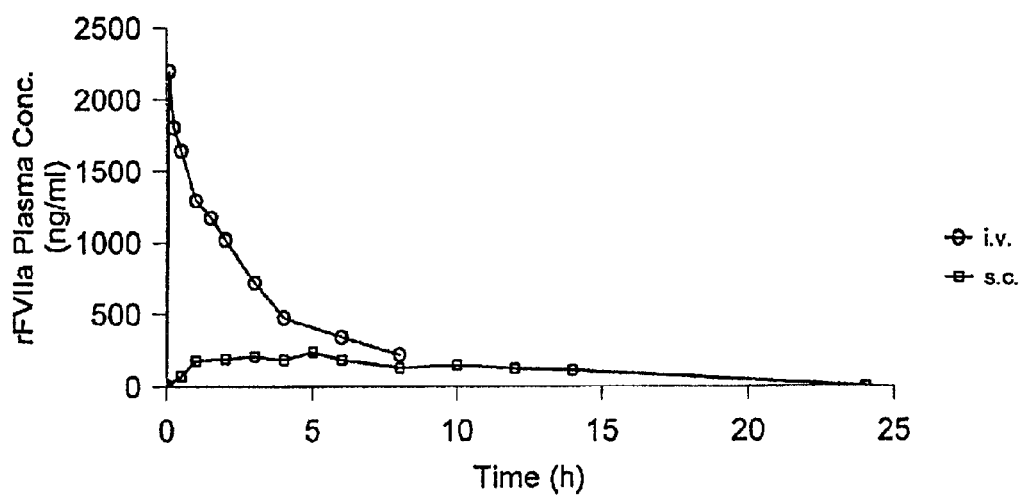

Figure 2. Individual Plasma Activity Profiles of rFVIIa Following Intravenous (i.v.) and Subcutanous (s.c.) Administration of 0.2 mg/kg to Minipigs
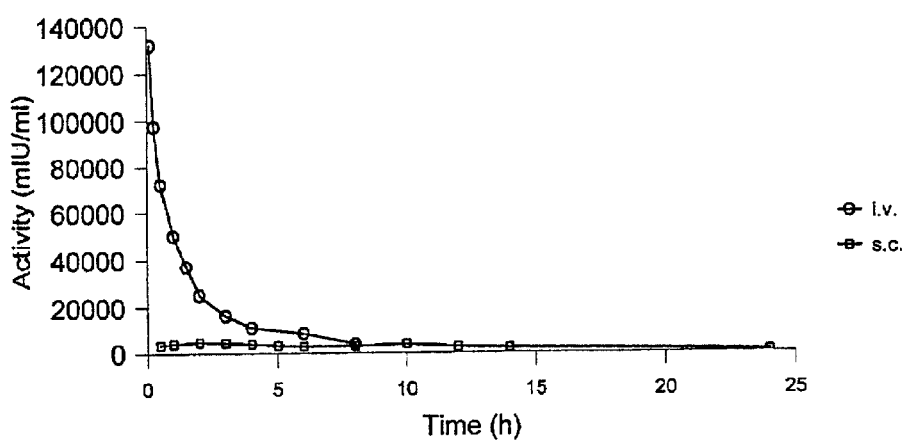
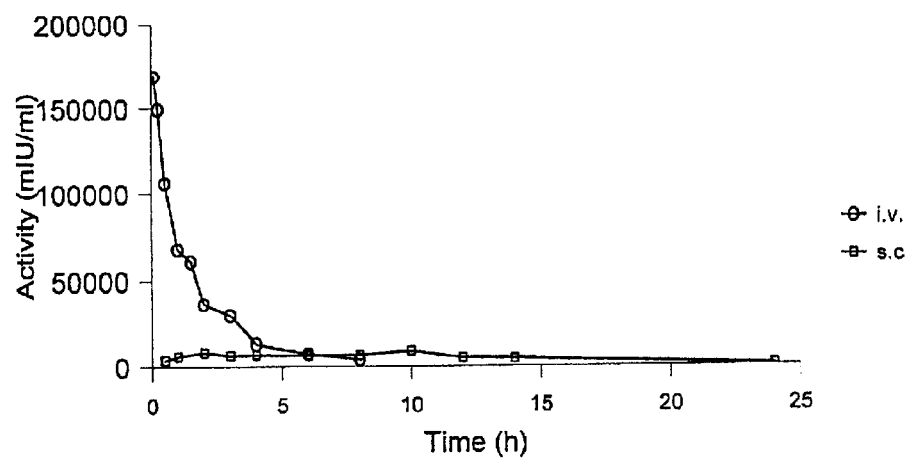

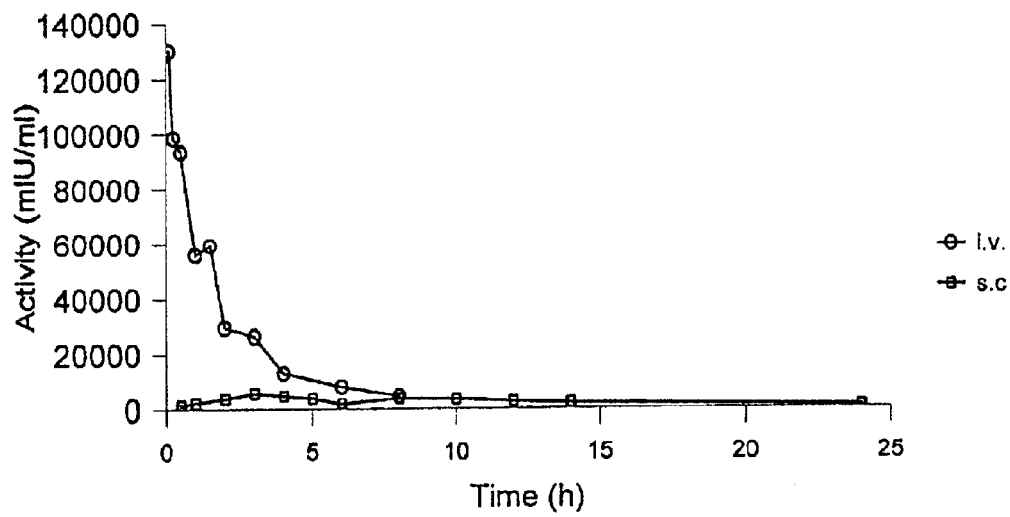
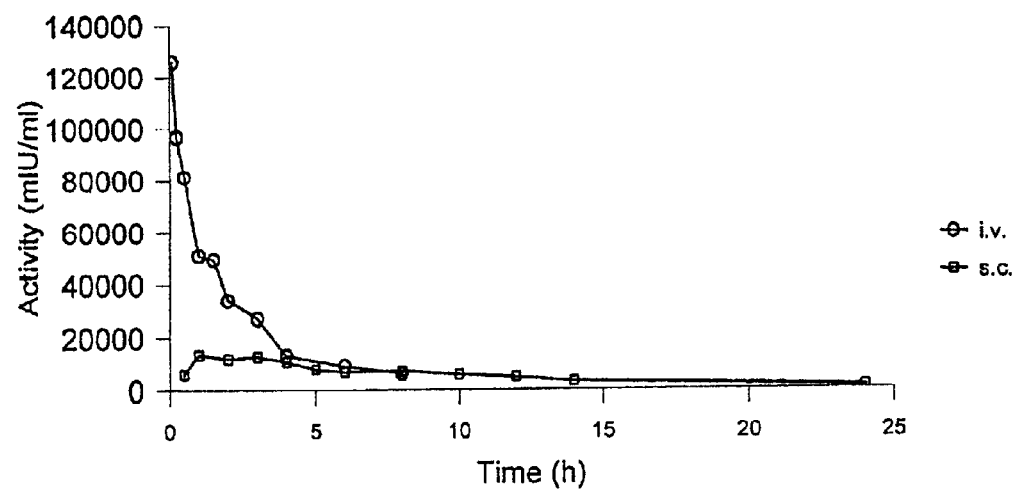

COAGULATION FACTOR VIIA COMPOSITION

CROSS REFERENCE TO RELATED APPLICATIONS

This application is a continuation of U.S. Ser. No. 09/148,440 filed on Sep. 4, 1998 now U.S. Pat. No. 6,310,183, and claims priority under 35 U.S.C. 119 of Danish application No. 1038/97 filed on Sep. 10, 1997, and U.S. provisional application No. 60/059,236 filed on Sep. 18, 1997, the contents of which are fully incorporated herein by reference.

FIELD OF INVENTION

The invention relates to pharmaceutical compositions for subcutaneous, intramuscular or intradermal administration of coagulation factor VIIa (FVIIa). The invention further relates to pharmaceutical compositions for prolonging the biological half-life of FVIIa in a mammal, preferably a human being by subcutaneous, intramuscular or intradermal injection. The invention also relates to a kit comprising FVIIa and a pharmaceutically acceptable carrier adapted for delivery of an effective dose of FVIIa to a patient in need thereof by subcutaneous, intramuscular or intradermal injection, a method of treatment of a disease affectable by FVIIIa, a method for prolonging the biological half-life of FVIIa in a mammal, and the use of FVIIa for the manufacture of said compositions.

BACKGROUND OF INVENTION

Blood coagulation is a process consisting of a complex interaction of various blood components, or factors, which eventually gives rise to a fibrin clot. Generally, the blood components which participate in what has been referred to as the coagulation "cascade" are proenzymes or zymogens, enzymatically inactive proteins which are converted to proteolytic enzymes by the action of an activator, itself an activated clotting factor. Coagulation factors that have undergone such a conversion are generally referred to as "active factors", and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, or pathways, that promote the activation of Factor X. The "intrinsic pathway" refers to those reactions that lead to thrombin formation through utilisation of factors present only in plasma. A series of protease-mediated activations ultimately generates Factor IXa which, in conjunction with Factor VIIIa, cleaves Factor X into Xa. An identical proteolysis is effected by Factor VIIa and its co-factor, tissue factor, in the "extrinsic pathway" of blood coagulation. Tissue factor is a membrane bound protein and does not normally circulate in plasma. Upon vessel disruption, however, it can complex with Factor VIIa to catalyse Factor X activation or Factor IX activation in the presence of $Ca^{++}$ and phospholipid (Nemerson and Gentry, *Biochem.* 25:4020–4033 (1986)). While the relative importance of the two coagulation pathways in haemostasis is unclear, in recent years Factor VII and tissue factor have been found to play a pivotal role in the regulation of blood coagulation.

Factor VII is a trace plasma glycoprotein that circulates in blood as a single-chain zymogen. The zymogen is catalytically inactive (Williams et al., *J. Biol. Chem.* 264:7536–7543 (1989); Rao et al., *Proc. Natl. Acad. Sci. USA.* 85:6687–6691 (1988)). Single-chain Factor VII may be converted to two-chain Factor VIIa by Factor Xa, Factor XIIa, Factor IXa or thrombin in vitro. Factor Xa is believed to be the major physiological activator of Factor VII. Like several other plasma proteins involved in haemostasis, Factor VII is dependent on vitamin K for its activity, which is required for the γ-carboxylation of multiple glutamic acid residues that are clustered in the amino terminus of the protein. These γ-carboxylated glutamic acids are required for the metal-associated interaction of Factor VII with phospholipids.

The conversion of zymogen Factor VII into the activated two-chain molecule occurs by cleavage of an internal peptide bond located approximately in the middle of the molecule. In human Factor VII, the activation cleavage site is at $Arg_{152}$-$Ile_{153}$ (Hagen et al., *Proc. Natl. Acad. Sci. USA* 83: 2412–2416 (1986); Thim et al., *Biochem.* 27:7785–7793 (1988) both of which are incorporated herein by references). Bovine Factor VII is activated by cleavage at the analogous $Arg_{152}$-$Ile_{153}$ bond (Takeya et al., *J. Biol. Chem.* 263: 14868–14877, 1988). In the presence of tissue factor, phospholipids and calcium ions, the two-chain Factor VIIa rapidly activates Factor X or Factor IX by limited proteolysis.

Coagulation factors are large proteins that are normally given intravenously to make the medicament directly available in the bloodstream. It would however be advantageous if a medicament could be given subcutaneously, intramuscularly or intradermally as these administration forms are much easier to handle for the patient, especially if the medicament must be taken regularly during the whole life and treatment is to start early, e.g. when the patient is a child. However, a medicament with a very large and labile molecule normally has a low bioavailability if given subcutaneously, intramuscularly or intradermally, since the uptake is low and degradation is severe. Furthermore, such large proteins may be immunogenic when administered subcutaneously.

Recombinant human Factor VIIa (rFVIIa) is an activated coagulation factor that is useful in the treatment of haemophiliacs that generate neutralising antibodies against Factor VIII or Factor IX. Factor VIII and Factor IX causes severe antibody formation in approximately 10% of the haemophilia patients. The action of rFVIIa (activation of the coagulation system via Factor X) is exerted in the vascular compartment of the body. The route of administration of rFVIIa has until now been intravenously. As a result of the relatively short half-life, administration normally has to be repeated every 2.5 to 3 hours. An alternative form of administration which would result in a reasonable bioavailability and a long lasting absorption phase would allow an increase in dosing intervals and at the same time make self administration possible, thus increasing the convenience for the patient.

Factor VIIa is known to be a glycoprotein with a molecular weight of approximately 50 kDa. It is therefore a sufficiently large molecule to point to the need for direct introduction into the bloodstream, since a very low bioavailability, if any, would be expected. Furthermore quite large doses may be required for an adult, for example during surgery. Consequently, Factor VIIa has conventionally been delivered intravenously to haemophilia A or B patients, either prophylactically or in response to bleeding episodes. Such repeated use of intravenous injections, while necessary to control the disease, has side effects. Repeated injections leads to the vein at the site of injection becoming fibrosed or occluded, a problem especially acute when treating the elderly. Also, when veins are small, as in babies, it may be difficult for the doctor to insert a needle into the vein to inject the required therapeutic dose.

To our knowledge, the only coagulation factor proteins which have been administered by subcutaneous injection is Factor VIII (170–300 kDa) and Factor IX (60 kDa). These coagulation factors, however, are administered in the form of the single-chain zymogens which are not yet activated. These non-activated forms are much more stable than the activated, cleaved forms which are degraded much faster. Subcutaneous injection does not significantly change the pharmacokinetic properties (especially half life) of these two proteins.

Surprisingly, it has now been found that the activated, cleaved and thus more labile form of Factor VII (FVIIa) can be delivered by subcutaneous, intramuscular or intradermal injection with sufficiently transport into the bloodstream in biologically active form and in adequate concentrations. This is especially surprising since FVIIa is tissue factor cofactor and thus would be expected to be caught in the tissues. It has also surprisingly been found that FVIIa shows favourable pharmacokinetic properties (especially half life) when injected subcutaneously, intramuscularly or intradermally.

We have thus developed a composition which makes it possible to administer Factor VIIa subcutaneously, intramuscularly or intradermally and which gives a great advantage for all patients in need of Factor VIIa. This opens the possibility of using FVIIa for prophylactic treatment of haemophilia patients that will thus avoid the risk of forming life threatening antibodies towards Factor VIII and Factor IX.

Factor VIIa is useful for administration to mammals, particularly humans, to control bleeding disorders, particularly bleeding disorders which are caused by clotting factor deficiencies (haemophilia A and B), or clotting factor inhibitors or bleeding disorders in patients not suffering from haemophilia A or B, for example, in patients suffering from von Willebrand's disease. Patients with von Willebrand's disease have a defective primary haemostasis because they lack or have an abnormal von Willebrand factor protein. Bleeding disorders are also seen in patients with a normally functioning blood clotting cascade and may be caused by a defective platelet function, thrombocytopenia, or even by unknown reasons. Furthermore, FVIIa may be used for preventing or treating excessive bleedings in patients where the haemostatic system including the coagulation cascade and platelets is functioning normally. Such excessive bleedings are, for example, bleedings in association with tissue damage, for example surgery or trauma, especially in tissues rich in tissue factor (TF). FVIIa may be used in such situations as well as when the bleeding is diffuse and poorly responding to current haemostatic techniques and therapies (e.g. haemorrhagic gastritis and profuse uterine bleeding). FVIIa may also be suitable for the treatment of bleedings occurring in organs with limited possibility for mechanical haemostasis such as brain, inner ear region, eyes as well as in association with the process of taking biopsies from various organs and in laparoscopic surgery.

Background art

International Patent Application No. WO 93/07890 relates to the treatment of haemophilia with FIX by subcutaneous injection.

International Patent Application No. WO 95/01804 relates to a coagulation Factor VIII formulation for treatment of haemophilia B.

International Patent Application No. WO 95/26750 relates to a formulation of FVIII or FIX suitable for subcutaneous injection for treatment of haemophilia A or B.

International Patent Application No. WO 95/28954 relates to concentrated preparations of FIX suitable for storage and subcutaneous injection.

BRIEF DESCRIPTION OF THE DRAWINGS

FIG. 1 shows the Individual Plasma Concentration Profiles of rFVIIa Following Intravenous (i.v.) and Subcutanous (s.c.) Administration of 0.2 mg/kg to Animals 1–4 (as indicated).

FIG. 2 shows the Individual Plasma Activity Profiles of rFVIIa Following Intravenous (i.v.) and Subcutanous (s.c.) Administration of 0.2 mg/kg to Animals 1–4 (as indicated).

LIST OF TABLES

Table 1 shows the PK-Results from ELISA-Assay following Dosing 0.2 mg/kg (0.33 ml/kg) rFVII i.v. and s.c. to Minipigs Weighing 11.4–13.4 kg.

Table 2 shows the PK-Results from Clot-Assay Following Dosing 0.2 mg/kg (0.33 ml/kg) rFVII i.v. and s.c. to Minipigs Weighing 11.4–13.4 kg.

SUMMARY OF THE INVENTION

It has now surprisingly been found that activated coagulation Factor VII, (Factor VIIa or FVIIa), which is a very sensitive protein, can be given subcutaneously, intramuscularly or intradermally, showing an acceptable absorption and a high level of active Factor VIIa protein in the blood. Furthermore, the plasma half life of both FVII antigen and FVII activity is increased significantly by the above administration and the t(max) is delayed by several hours.

One aspect of the invention is a pharmaceutical composition for subcutaneous, intramuscular or intradermal administration comprising coagulation factor VIIA. Another aspect of the present invention is a pharmaceutical composition for prolonging the biological half-life of FVIIa in a mammal, comprising FVIIa and a pharmaceutical acceptable carrier adapted for delievery of an effective dose of FVIIa to a patient in need thereof by subcutaneous, intramuscular or intradermal injection. Another aspect of the invention is a method for treatment of a disease affectable by FVIIa by subcutaneously, intramuscularly or intradermally administering to a patient in need thereof a composition comprising FVIIa. A further aspect is a kit comprising FVIIa and a pharmaceutically acceptable carrier adapted for delivery of an effective dose of FVIIa to a patient in need thereof by subcutaneous, intramuscular or intradermal injection. Another aspect is the use of FVIIa for the manufacture of a composition for subcutaneous, intramuscular or intradermal administration for treatment of diseases affectable by FVIIa. Another aspect is a method for prolonging the biological half-life of FVIIa in a mammal, comprising administering FVIIa by subcutaneous, intramuscular or intradermal injection to a mammal in need thereof. A further aspect is the use of FVIIa for the manufacture of a composition for subcutaneous, intramuscular or intradermal administration for prolonging the biological half-life of FVIIa in a mammal.

A preferred embodiment is where the composition according to the invention is administered subcutaneously. In another preferred embodiment the FVIIa is recombinant human FVIIa. In still another preferred embodiment the mammal in need of administration of FVIIa is a human being.

DETAILED DESCRIPTION OF THE INVENTION

Definitions

Factor VIIa, or FVIIa, may be purified from blood or produced by recombinant means. It is evident that the practice of the methods described herein is independent of how the purified Factor VIIa is derived and, therefore, the present invention is contemplated to cover use of any Factor VIIa preparation suitable for use herein.

In this context, the term "Factor VII", or "FVIIa", is designated to include authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

In this context, the term "a FVIIa unit" is defined by calibration against a secondary standard of the First International Standard 89/688 established in 1993. 50 international units (IU) FVIIa correspond to about 1 µg protein.

In this context, the term "treatment" is designated to include prophylactic treatment of a FVIIa affectable disease.

Abbreviations

| | |
|---|---|
| TF | tissue factor |
| FVII | factor VII in its single-chain, unactivated form |
| FVIIa | factor VII in its activated form |
| rFVIIa | recombinant factor VII in its activated form |
| FVIII | factor VIII in its unactivated form |
| FIX | factor IX in its unactivated form |
| IU | International Units |

Preparation of Compound

Human purified factor VIIa suitable for use in the present invention is preferably made by DNA recombinant technology, e.g. as described by Hagen et al., *Proc.Natl.Acad.Sci. USA* 83: 2412–2416, 1986 or as described in European Patent No. 200.421 (ZymoGenetics). Factor VIIa produced by recombinant technology may be authentic factor VIIa or a more or less modified factor VIIa provided that such factor VIIa has substantially the same biological activity for blood coagulation as authentic factor VIIa. Such modified factor VIIa may be produced by modifying the nucleic acid sequence encoding factor VII either by altering the amino acid codons or by removal of some of the amino acid codons in the nucleic acid encoding the natural FVII by known means, e.g. by site-specific mutagenesis.

Factor VII may also be produced by the methods described by Broze and Majerus, *J.Biol.Chem.* 255 (4): 1242–1247, 1980 and Hedner and Kisiel, *J.Clin.Invest.* 71: 1836–1841, 1983. These methods yield factor VII without detectable amounts of other blood coagulation factors. An even further purified factor VII preparation may be obtained by including an additional gel filtration as the final purification step. Factor VII is then converted into activated FVIIa by known means, e.g. by several different plasma proteins, such as factor XIIa, IX a or Xa. Alternatively, as described by Bjoern et al. (Research Disclosure, 269 September 1986, pp. 564–565), factor VII may be activated by passing it through an ion-exchange chromatography column, such as Mono Q® (Pharmacia fine Chemicals) or the like.

Pharmaceutical Administration

The regimen for any patient to be treated with FVIIa as mentioned herein should be determined by those skilled in the art. The dose to be administered in therapy can be determined by a physician and will depend on the route of administration (subcutaneous, intramuscular or intradermal) and on the weight and the condition of the patient.

Where FVIIa injected intravenously has to be given every second hour, FVIIa injected subcutaneously, intradermally or intramuscularly should be administered with an interval of 12–48 hours, preferably 24 hours. FVIIa is preferably administered by subcutaneous injections and in an amount of about 100–100,000 units per kg body weight, and preferably in an amount of about 250–25,000 units per kg body weight corresponding to about 5–500 µg/kg.

Pharmaceutical Compositions

An intravenous injection is normally 5–20 ml. It is normally preferred that an injection given subcutanously is between 0.05 to 1 ml. The concentration of FVIIa must therefore be high in such a formulation.

The volume given can be more than 0.01 ml, suitable 0.1–2 ml, preferably 0.25–1.5 ml and more preferable 0.5–1 ml.

Additives increasing the bioavailability of FVIIa are suitably organic compounds per se, salts thereof, emulsions or dispersions containing organic compounds per se or salts thereof, e.g. dispersions of polar lipids, or any combination or sequence of addition thereof. Organic compounds useful in the invention are e.g. amino acids, peptides, proteins, and polysaccharides. Peptides include dipeptides, tripeptides, oligopeptides, such as collagen and gelatine. The collagen and gelatine is preferably hydrolysed. Polysaccharides include e.g. chitosans, cyclodextrins, starch, hyaluronic acids, dextrans, cellulose, and any derivatives, combinations and/or sequence of addition thereof. The starch is preferably hydrolysed. The emulsions include oil-in-water emulsions with oil as the dispersed phase and water-in-oil dispersions with oil as the continuous phase. The oil can be of vegetable or animal origin or synthetically produced. Suitably, the vegetable oil of the emulsions is soybean oil or safflower oil, or any combination thereof. Suitably the polar liquids are one or more phospho-lipids or glycolipids or any combination thereof. The additives increasing the bioavailability of FVIIa could be added to the formulation before drying or upon reconstitution, or it could be added to a stable solution or dispersion containing FVIIa.

Before administration, one or more aqueous solutions or dispersions could be added, in any mixture or sequence, to a formulation according to the present invention, which is a stable aqueous solution, a dispersion or in dried form.

The formulation could be in a dried form, preferably freeze-dried. Before administration, the dried product can be reconstituted with an aqueous solution or a dispersion e.g. a suspension, a liposomal formulation or an emulsion.

The formulation can also be a stable aqueous solution ready for administration. It can also be a dispersion, e.g. a suspension, a liposomal formulation or an emulsion.

The composition is preferably given subcutanously. The FVIIa activity in the formulation is preferably from about 0.1 mg/ml to about 50 mg/ml, more preferred from about 0.3 mg/ml to about 25 mg/ml, more preferred from about 0.6 mg/ml to about 25 mg/ml, more preferred from about 0.6 mg/ml to about 15 mg/ml, more preferred from about 1 mg/ml to about 15 mg/ml, and even more preferred from about 3 mg/ml to about 15 mg/mi.

The formulation may also comprise salt in order to give an isotonic solution, e.g. NaCl, KCl, and/or it may comprise one or more other isotonicity establishing compounds, preferably in an amount of more than 1.0 mg/ml.

Calcium, or other divalent metal ions, e.g. zinc, is necessary for the maintenance of the FVIIa activity. It may be added as, for example, calcium chloride, but other salts such as calcium gluconate, calcium glubionate or calcium gluceptate may also be used. The composition preferable comprises calcium chloride in an amount of more than 0.15 mg/ml.

An amino acid is preferably used to buffer the system and it also protects the protein if the formulation is freeze-dried. A suitable buffer could be glycine, lysine, arginine, histidine or glycylglycine, preferred is glycylglycine.

A non-ionic surfactant may also be present in the composition. The surfactant is preferable chosen from block-copolymers, such as a poloxamer, e.g. poloxamer 188, or a polyoxyethylene sorbitan fatty acid ester, such as polyoxyethylene-(20)-sorbitan monolaurate or polyoxyethylene-(20)-sorbitan monooleate. Preferred are polyoxyethylene-(20)-sorbitan monooleate (Tween 20). Tween 20) is preferably used in a concentration of at least 0.01 mg/ml. The non-ionic surfactant, if used, should preferably be present in an amount above the critical micelle concentration (CMC). See Wan and Lee, Journal of Pharm Sci, 63, p. 136, 1974.

Mono- or disaccharides (e.g. sucrose), polysaccharides such as low molecular weight dextrins, or sugar alcohols (e.g. sorbitol, glycerol or mannitol) may be added. The composition may also comprise antioxidants such as bisulfite, ascorbate gluthathione, acetylcystein, tocopherol, methionin, EDTA, citric acid, butyl hydroxy toluene and /or butyl hydroxy anisole. Complexing agents, such as EDTA and citric acid can also be present in small concentrations for stabilising the FVIIa molecules, if they exhibit a stronger affinity for destabilising metal ions than for calcium or other divalent metal ions, e.g. zn2+. Furthermore, preservatives such as benzyl alcohol, phenol, sorbic acid, parabens, and chlorocresol may be added.

The adjuvants are generally present in a concentration of from 0.001 to 4% w/v. The pharmaceutical preparation may also contain protease inhibitors, e.g. aprotinin.

The pH of the preparation is preferably adjusted to a value in the interval of 2–9.

Preparations having a pH from about 5.0 to about 7.5 are preferred, more preferred are preparations having a pH from about 5.0 to about 6.0, most preferred are preparations having a pH about 5.5.

Our used FVIIa is highly purified, i.e. has a specific activity of more than 40 IU/μg.

| A preferred composition consists of | |
|---|---|
| rFVIIa | 0.6 mg/ml (30,000 IU/ml) |
| Sodium chloride | 2.92 mg/ml |
| Glycylglycine | 1.32 mg/ml |
| Polysorbate 80 | 0.07 mg/ml |
| Calcium chloride, 2H2O | 1.47 mg/ml |
| Mannitol | 30.00 mg/ml |
| pH 5.5 | |

(reconstituted with st6rile water to 1 ml)

Conventional techniques for preparing pharmaceutical compositions which can be used according to the present invention are, for example, described in *Remington: The Science and Practice of Pharmacy*, 19th ed., 1995.

The compositions may be sterilised by, for example, filtration through a bacteria-retaining filter, by incorporating sterilising agents into the compositions, by irradiating the compositions, or by heating the compositions. They can also be manufactured in the form of sterile solid compositions which can be dissolved in sterile water, or some other sterile injectable medium prior to or immediately before use.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Materials and Methods

The production of recombinant Factor VIIA (rFVIIa) was essentially performed as described in European Patent No. 200,421.

The FVIIa activity and the concentration were adjusted by dilution with water for injection and excipients were added in suitable amounts. The solution was then sterile filtered and freeze-dried.

| Lyophilised powder of rFVIIa: | |
|---|---|
| rFVIIa | 0.6 mg/ml |
| Sodium chloride | 2.92 mg/ml |
| Glycylglycine | 1.32 mg/ml |
| Polysorbate 80 | 0.07 mg/ml |
| Calcium chloride, 2H2O | 1.47 mg/ml |
| Mannitol | 30.00 mg/ml |
| pH 5.5 | |

Prior to use, the lyophilised composition was reconstituted in water to a total volume of 1.0 ml.

Example 1

Animals

The study was performed in 4 female Göttingen minipigs from Ellegaard Göttingen Minipigs ApS, Sorø Landevej 302, DK-4261, Dalmose, Denmark. At start of the acclimatisation period the animals were 7 to 8 months old and the body weight was in the range 11.2 to 13 kg. A predosing period of one week (including an acclimatisation period of 5 days) was allowed before dosing.

Twice daily the animals were offered water and food (175 g Altromin 9023 for the first 2 days, thereafter 200 g).

The study was performed in a thermostated room at 21±3° C.

Drugs and Chemicals rFVIIa was used for dosing. The substance was dissolved in sterile $H_2O$ to give 0.6 mg/ml. All other chemicals were obtained from commercial sources and were of analytical grade.

Experimental Design

The animals were dosed once intravenously (i.v.) and once subcutanously (s.c.) separated by a wash-out period of one week as follows:

| | Route of dosing | |
|---|---|---|
| Animal No. | First dosing | Second dosing |
| 1 | s.c. | i.v. |
| 2 | s.c. | i.v. |
| 3 | i.v. | s.c. |
| 4 | i.v. | s.c. |

The dose was 0.2 mg/kg body weight corresponding to 0.33 ml/kg body weight.

The i.v. dose was given via a needle or a short catheter in an ear vein. Immediately after dosing the needle/catheter was flushed with 2–5 ml sterile, isotonic water.

The s.c. dose was given behind the pinna. The area of the dosing was marked with a colour marker.

Blood and Tissue Sampling

Blood samples were collected via needle puncture of the jugular vein/bijugular trunk. In connection with i.v. dosing the samples were collected before, and 6, 15, 30, 60 and 90 minutes and 2, 3, 4, 6 and 8 hours after dosing. Following s.c. dosing the samples were collected at 30, 60 minutes and 2, 3, 4, 5, 6, 8, 10, 12 14 and 24 hours as well as before dosing.

All blood samples were taken within 1 minute from stipulated time except for two samples (animal no. 4, 14 and 24 hours after s.c. dosing) that were taken 2 minutes after scheduled time.

The blood samples (3 ml) were collected in Vacutainers containing citrate for stabilisation and kept in ice-water until centrifugation (10 min, +40° C., about 1268×G). Two aliquots each of 150 TI were taken from each sample. To one of the aliquots 1350 TI of the buffer used for ELISA assay were added and the mixture devided between two Nunc Cryotubes labelled with "ELISA" appart from identification and stored at approximately −20° C. pending transfer to the Immunochemistry deparment for assay. To the other aliquot 1350 µl of the buffer used for Clot assay were added and the mixture devided between two Nunc Cryotubes. The tubes were labelled with "CLOT" apart from identification and stored at −80° C. pending transfer to the Immunochemistry department, Novo Nordisk, for assay. Buffer was added to the samples within 0.5 h after sampling and the samples were frozen within 1 h after sampling.

The day after the second dosing all animals were anaesthetized with an i.p. injection of mebumal and killed by exsanguination. The subcutaneous injection sites were located, examined macroscopically and representative samples were removed and fixed in phosphate buffered neutral 4% formaldehyde and transferred to the Pathology department, Novo Nordisk, for histopatological examination.

Analytical Methods

The concentration of rFVIIa was determined by an ELISA and the activity of rFVIIa by a Clot assay.

ELISA

The ELISA assay was FVII:Ag ELISA performed as described in Kit insert no. 1994.09/db version 1.0 (Danish version). The assay has previously been validated for human and rat plasma. A preliminary validation showed no indication of problems by using the assay for analysis in pig plasma.

The assay is a two-site monoclonal immunoenzymatic assay using peroxidase as the marker enzyme. The microtiter wells are precoated with a specific anti-factor VII monoclonal antibody. Thereafter both sample and enzyme-labelled antibody are added to the well. During the following step, a "sandwich" is formed between the solid-phase antibody, the Factor VII molecule and the enzyme-labelled specific Factor VII monoclonal antibody. Following a washing step, where unbound enzyme-labelled antibody is remove, the activity of the bound peroxidase is measured by enzyme's ability to transform a colourless substrate to a coloured product. The colour development is stopped by addition of sulphuric acid and is measured at 492 nm. As standard is used rFVIIa delivered with the assay. The calibration of the standard is based on absorbency measurement at 280 nm.

Clot-assay

The Clot-assay was FVIIa:Clot (Stago) performed according to the kit insert. The assay has previously been validated for human and rat plasma. A preliminary validation showed no indication of problems by using the assay for analysis in pig plasma.

The recombinant soluble tissue factor (rsTF) possesses a cofactor function specific for FVIIa. Consequently the FVII present in the test plasma does not interfere in the assay. The rsTF in the presence of FVIIa, phospholipids and $Ca^{++}$ produces coagulation of plasma. The observed clotting time bears an inverse relationship with the FVIIa level initially present in plasma. As standard is used rFVIIa delivered with the assay. The calibration of the standard is based on a comparison with the international FVIIa standard.

Analysis of Data

Results from ELISA as well as from Clot assay were subjected to non-compartmental pharmacokinetic analysis using the PC-based software WinNonlin (Scientific Consulting Inc.).

Results and Discussion

Results from the ELISA and Clot assays are given in Appendix A. Individual plasma concentration profiles are given in FIGS. 1 and 2. while individual pharmacokinetic parameters are given in Tables 1 and 2.

None of the predose samples had measurable concentrations or activities indicating sufficient wash-out between the two dosing periods.

The plasma concentration and activity profiles (FIG. 1–2) show an extended absorption phase following s.c. administration resulting in a $t_{max}$ mean of 6.5 (range 5–8 hours) and 4.0 (range 1.0–10.0) for concentration and activity, respectively.

TABLE 1

PK-Results from ELISA-Assay following Dosing 0.2 mg/kg (0.33 ml/kg) rFVII i.v. and s.c. to Minipigs Weighing 11.4–13.4 kg

| Animal No. | $C_{max}$ (ng/ml) | | $t_{max}$ (h) | $AUC_{0-\infty}$ (ng · h/ml) | | Extrapol. AUC (%) | | f (%) | Half-life (h) | |
|---|---|---|---|---|---|---|---|---|---|---|
| | i.v. | s.c. | s.c. | i.v. | s.c. | i.v. | s.c. | s.c. | i.v. | s.c. |
| 1 | 2130 | 86.3 | 8.0 | 4980 | 1711 | 11.2 | 14.7 | 34.4 | 2.7 | 7.7 |
| 2 | 2447 | 245.0 | 8.0 | 6960 | 4195 | 14.7 | 12.1 | 60.0 | 3.3 | 6.5 |
| 3 | 2134 | 142.6 | 5.0 | 6414 | 1849 | 13.0 | 12.7 | 28.8 | 2.9 | 7.2 |
| 4 | 2200 | 233.8 | 5.0 | 6659 | 2903 | 16.4 | 5.4 | 43.6 | 3.5 | 4.8 |
| Mean | 2228 | 176.9 | 6.5 | 6261 | 2665 | 13.8 | 11.2 | 41.7 | 3.5[a] | 6.4[a] |
| SD | 150 | 75.9 | 1.7 | 886 | 1151 | 2.3 | 4.0 | 13.6 | | |

[a]Harmonic mean

TABLE 2

PK-Results from Clot-Assay Following Dosing 0.2 mg/kg (0.33 ml/kg)
rFVII i.v. and s.c. to Minipigs Weighing 11.4–13.4 kg

| Animal No. | $C_{max}$ (mIU/ml) i.v. | $C_{max}$ (mIU/ml) s.c. | $t_{max}$ (h) s.c. | $AUC_{0-\infty}$ (mIU·h/ml) i.v. | $AUC_{0-\infty}$ (mIU·h/ml) s.c. | Extrapol. AUC (%) i.v. | Extrapol. AUC (%) s.c. | f (%) s.c. | Half-life (h) i.v. | Half-life (h) s.c. |
|---|---|---|---|---|---|---|---|---|---|---|
| 1 | 161454 | 4609 | 2.0 | 201887 | 67038 | 7.0 | 11.4 | 33.2 | 2.6 | 6.9 |
| 2 | 183766 | 9155 | 10.0 | 274157 | 126227 | 4.9 | 5.0 | 46.0 | 2.3 | 4.7 |
| 3 | 156908 | 5415 | 3.0 | 240033 | 63730 | 6.7 | 12.0 | 26.6 | 2.6 | 7.0 |
| 4 | 149559 | 13355 | 1.0 | 249408 | 135294 | 12.4 | 8.1 | 54.2 | 3.6 | 6.4 |
| Mean | 162922 | 8134 | 4.0 | 241371 | 98073 | 7.8 | 9.1 | 40.0 | 2.7[a] | 6.1[a] |
| SD | 14735 | 4005 | 4.1 | 30001 | 37950 | 3.2 | 3.2 | 12.4 | | |

[a]Harmonic mean

Consequently, $C_{max}$ values were greatly reduced compared to those following i.v. administration (Tables 1 and 2). The AUCs following s.c. administration were reduced compared to those following i.v. administration (Tables 1 and 2). However, the extent of bioavailability was reasonably good as the mean f was 41.7% (range 28.8–60.0%) and 40.0% (range 26.6–54.2%) as estimated from ELISA and Clot assay results, respectively.

The half-life following s.c. administration was for all animals and for concentration as well as for activity results increased compared to that after i.v. administration (Table 1 and 2) The reason for that is most likely the so called "flip-flop" meaning that the rate of absorption is more slow than the rate of elimination. The half-life following s.c. administration is therefore a measure of the absorption rate rather than of the elimination rate.

Conclusion

The bioavailability of rFVIIa following subcutaneous administration to minipigs was sufficiently high to make this route of administration interesting in man. The absorption phase following s.c. administration was prolonged to an extent that might allow significantly increased dosing intervals in humans compared to those needed in connection with i.v. administration.

TABLE 3 rFVII Plasma Concentration and Activity Data

| | Results from ELISA (ng/ml) | | | | Results from Clot assay (mIU/ml) | | | |
|---|---|---|---|---|---|---|---|---|
| | Pig 1 | Pig 2 | Pig 3 | Pig 4 | Pig 1 | Pig 2 | Pig 3 | Pig 4 |
| I.v. Adm. Time (h) | | | | | | | | |
| 0 | <[a] | <[a] | <[a] | <[a] | <[b] | <[b] | <[b] | <[b] |
| 0.1 | 2129.9 | 2447.2 | 2134.1 | 2200 | 131950 | 169150 | 130260 | 125680 |
| 0.25 | 1713.9 | 2058.5 | 1921.7 | 1810.2 | 97488 | 149376 | 98528 | 96816 |
| 0.5 | 1389.5 | 1801.4 | 1699.7 | 1639.3 | 72332 | 106160 | 93384 | 81248 |
| 1 | 1151.5 | 1285.2 | 1336.5 | 1291.7 | 50155 | 67885 | 55860 | 50855 |
| 1.5 | 869.1 | 1157.9 | 1134.5 | 1167.8 | 36960 | 60625 | 59352 | 49193 |
| 2 | 669.4 | 1306.5 | 1023.2 | 1019.9 | 25011 | 36475 | 29230 | 33830 |
| 3 | 586.7 | 731.5 | 718.9 | 717.5 | 16349 | 29708 | 26200 | 26675 |
| 4 | 410.2 | 515.7 | 524.7 | 472.1 | 11149 | 13514 | 12923 | 12913 |
| 6 | 217.2 | 319.9 | 290.4 | 338.7 | 8641 | 7484 | 7812 | 9019 |
| 8 | 144.8 | 219.8 | 200.7 | 215.1 | 3813 | 4062 | 4364 | 5969 |
| s.c. Adm. Time (h) | | | | | | | | |
| 0 | <[a] | <[a] | <[a] | <[a] | <[b] | <[b] | <[b] | <[b] |
| 0.5 | <[a] | 45.9 | <[a] | 68.6 | 3263 | 3889 | 1118 | 5904 |
| 1 | 53.5 | 84 | <[a] | 171.7 | 3907 | 6293 | 1990 | 13355 |
| 2 | 74.2 | 159.1 | 54.3 | 185.1 | 4609 | 8568 | 3509 | 11943 |
| 3 | 79.2 | 156.8 | 97.5 | 202.6 | 4315 | 6744 | 5415 | 12707 |
| 4 | 77.1 | 184.1 | 104.2 | 178.6 | 3889 | 7020 | 4510 | 10743 |
| 5 | 67.3 | 192.3 | 142.6 | 233.8 | 3108 | n.s. | 3589 | 7720 |
| 6 | 71.6 | 224 | <[a,c] | 178.6 | 2740 | 6663 | 1642 | 6591 |
| 8 | 86.3 | 245 | 109.8 | 122.7 | 2884 | 6927 | 3585 | 7000 |
| 10 | 79.8 | 225.8 | 91.9 | 140.4 | 3867 | 9155 | 3310 | 5630 |
| 12 | 58.4 | 193.3 | 69.9 | 118.6 | 2542 | 4983 | 2555 | 4700 |

TABLE 3-continued rFVII Plasma Concentration and Activity Data

| | Results from ELISA (ng/ml) | | | | Results from Clot assay (mIU/ml) | | | |
|---|---|---|---|---|---|---|---|---|
| | Pig 1 | Pig 2 | Pig 3 | Pig 4 | Pig 1 | Pig 2 | Pig 3 | Pig 4 |
| 14 | 75.6 | 161.9 | 60.5 | 106.6 | 2066 | 4543 | 1977 | 2970 |
| 24 | 22.5 | 54.4 | 22.5 | 22.5 | 764 | 929 | 759 | 1180 |

[a]Below limit of quantitation (45 ng/ml)
[b]Below limit of quantitation (117.6 mIU/ml)
[c]Excluded as outliner
n.s. No sample

What is claimed is:

1. A method for treatment of a disease affectable by Factor VIIa (FVIIa), said method comprising administering subcutaneously to a mammal in need thereof an effective amount for treating said disease of a composition comprising modified FVIIa.

2. The method of claim 1 wherein the disease is haemophilia A or B.

3. The method of claim 1 wherein the modified Factor VIIa is modified human Factor VIIa that has been produced recombinantly.

4. The method of claim 1 wherein the composition is a stable aqueous solution ready for administration.

5. The method of claim 1 wherein the composition is dried and reconstituted with a pharmaceutically acceptable vehicle suitable for injection prior to administration.

6. A method for prolonging the biological half-life of Factor VIIa (FVIIa) being administered to a mammal, said method comprising administering to a mammal in need thereof by subcutaneous injection a composition comprising modified FVIIa.

7. The method of claim 6 wherein said mammal suffers from haemophilia A or B.

8. The method of claims 6 wherein the Factor VIIa is modified human Factor VIIa that has been produced recombinantly.

9. The method of claim 6 wherein the composition is a stable aqueous solution ready for administration.

10. The method of claim 6 wherein the composition is dried and reconstituted with a pharmaceutically acceptable vehicle suitable for injection prior to administration.

* * * * *

UNITED STATES PATENT AND TRADEMARK OFFICE
CERTIFICATE OF CORRECTION

PATENT NO.       : 6,833,352 B2
APPLICATION NO.  : 10/026032
DATED            : December 21, 2004
INVENTOR(S)      : Johannessen et al.

It is certified that error appears in the above-identified patent and that said Letters Patent is hereby corrected as shown below:

In the Title: "COAGULATION FACTOR VIIA COMPOSITION"
should read --COAGULATION FACTOR VIIa COMPOSITION--.
Column 1, lines 1-2: "COAGULATION FACTOR VIIA COMPOSITION"
should read --COAGULATION FACTOR VIIa COMPOSITION--.
Column 13, line 18, claim 1: "VHa (FV11a)" should read --VIIa (FVIIa)--.

Signed and Sealed this

Thirty-first Day of July, 2007

JON W. DUDAS
*Director of the United States Patent and Trademark Office*